(12) United States Patent
Zhang et al.

(10) Patent No.: US 6,683,194 B2
(45) Date of Patent: Jan. 27, 2004

(54) TOCOPHEROL DERIVATIVES

(75) Inventors: Yuehua Zhang, Mill Creek, WA (US); Manjari Lal, Bellevue, WA (US); Nagesh Palepu, Mill Creek, WA (US)

(73) Assignee: Sonus Pharmaceuticals, Inc., Bothell, WA (US)

( * ) Notice: Subject to any disclaimer, the term of this patent is extended or adjusted under 35 U.S.C. 154(b) by 72 days.

(21) Appl. No.: 10/068,806

(22) Filed: Feb. 5, 2002

(65) Prior Publication Data

US 2003/0149099 A1 Aug. 7, 2003

(51) Int. Cl.[7] ............................................. C07D 311/76
(52) U.S. Cl. ........................ 549/410; 424/489; 424/498; 424/502
(58) Field of Search ..................... 549/410; 424/489, 424/498, 502

(56) References Cited

U.S. PATENT DOCUMENTS 5,234,695 A  * 8/1993  Hobbs et al. ............... 424/489
5,891,469 A  * 4/1999  Amselem .................... 424/451
6,045,826 A     4/2000  Borowy-Borowski et al.
6,191,172 B1    2/2001  Borowy-Borowski et al.
6,458,373 B1 * 10/2002  Lambert et al. ............ 424/405

FOREIGN PATENT DOCUMENTS

EP        1 034 839 A1    9/2000

* cited by examiner

Primary Examiner—Alan L. Rotman
Assistant Examiner—Raymond Covington
(74) Attorney, Agent, or Firm—Christensen O'Connor Johnson Kindness PLLC

(57) ABSTRACT

Tocopherol derivatives are provided. In one embodiment, the tocopherol derivative includes a tocopherol moiety covalently coupled to branched hydrophilic moiety. In another embodiment, the tocopherol derivative includes a first tocopherol moiety covalently coupled to a second tocopherol moiety through a hydrophilic moiety. In other embodiments, the derivative includes three or more tocopherol moieties.

64 Claims, 12 Drawing Sheets

R:  -(CH$_2$CH$_2$CH$_2$CH)$_3$-CH$_3$ (with CH$_3$ branch)
X:  -COCH$_2$CH$_2$COO- R: -(CH₂CH₂CH₂CH)₃-CH₃ (with CH₃ branch)

X: -COCH₂CH₂COO-

R: -(CH$_2$CH$_2$CH$_2$CH(CH$_3$))$_3$-CH$_3$
X: -COCH$_2$CH$_2$COO-

R: -(CH$_2$CH$_2$CH$_2$CH)$_3$-CH$_3$
        |
        CH$_3$

X: -COCH$_2$CH$_2$COO-

R: -(CH$_2$CH$_2$CH$_2$CH(CH$_3$))$_3$-CH$_3$
X: -COCH$_2$CH$_2$COO-

R: -(CH$_2$CH$_2$CH$_2$CH)$_3$-CH$_3$ with CH$_3$ branch
X: -COCH$_2$CH$_2$COOns)# TOCOPHEROL DERIVATIVES

FIELD OF THE INVENTION

The present invention relates to tocoperol derivatives and, more particularly, to tocopherol derivatives in which a tocopherol moiety is covalently coupled to a branched hydrophilic moiety.

BACKGROUND OF THE INVENTION

Surfactants are molecules that are composed of groups of opposing solubility properties. The presence of two structurally dissimilar groups within a single molecule is a defining characteristic of surfactants. Surfactants typically include hydrophobic and hydrophilic groups. In contrast to cationic and anionic surfactants, nonionc surfactants are electronically neutral molecules that do not have a discrete charge when dissolved in aqueous media. The hydrophilicity of nonionic surfactants is provided by hydrogen bonding of the surfactant's hydrophilic group with water molecules. The hydrophilic groups of the surfactant often include oxygen atoms. Common nonionic surfactants include poly-oxyethylene surfactants.

In addition to the hydrophilic portion, the hydrophobic portion of a surfactant can be chosen to achieve the desired surfactant properties. While hydrocarbon chains are a common hydrophobic group, a surfactant's hydrophobic group can include a variety of organic groups that are relatively hydrophobic.

Tocopherol succinate polyethylene glycol (TPGS) is an example of a nonionic surfactant that includes a tocopherol (vitamin E) hydrophobic group and a poly(oxyethylene) hydrophilic group. While TPGS has been utilized in a variety of surfactant applications, there exists a need for surfactants having improved properties, including surfactants that include tocopherol-based hydrophobic groups and poly(oxyethylene) hydrophilic groups. The present invention seeks to fulfill this need and provides further related advantages.

SUMMARY OF THE INVENTION

In one aspect of the invention, a tocopherol derivative is provided. In one embodiment, the tocopherol derivative includes a tocopherol moiety covalently coupled to branched hydrophilic moiety. In another embodiment, the tocopherol derivative includes a first tocopherol moiety covalently coupled to a second tocopherol moiety through a hydrophilic moiety. In other embodiments, the derivative includes three or more tocopherol moieties.

In other aspects of the invention, methods for preparing and using the tocopherol derivatives are provided.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
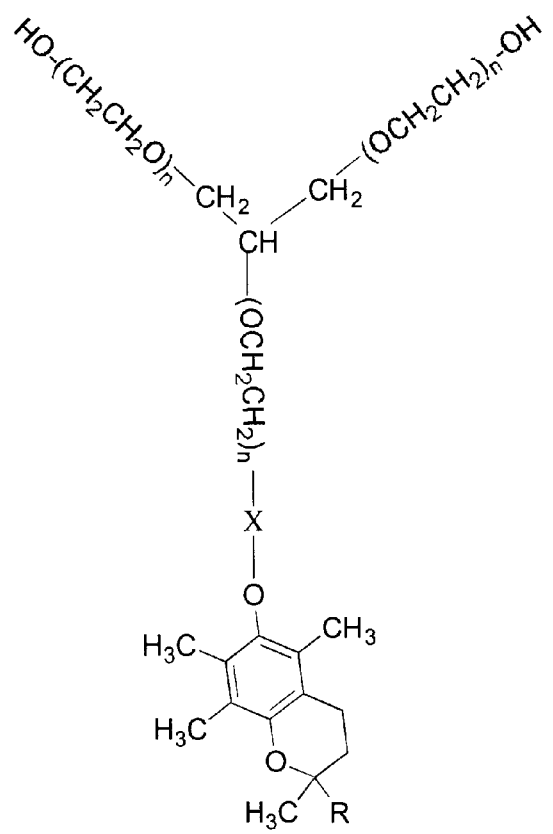
FIG. 1 is the structure of a representative tocopherol derivative of the present invention including a tocopherol moiety linked to a branched poly(oxyethylene)-containing hydrophilic moiety.

In one aspect of the invention, a tocopherol derivative is provided. In one embodiment, the tocopherol derivative includes a tocopherol moiety covalently coupled to branched hydrophilic moiety. In another embodiment, the tocopherol derivative includes two or more tocopherol moieties covalently linked though one or more hydrophilic moieties. In one embodiment, a first tocopherol moiety is covalently coupled to a second tocopherol moiety through a hydrophilic moiety. The tocopherol moiety or moieties of the derivative are relatively hydrophobic, and their combination with one or more hydrophilic moieties provides a tocopherol derivative having surfactant properties. Accordingly, because of their surfactant properties, the tocopherol derivatives of the invention can be used as surfactants in a variety uses as described below. As surfactants, the tocopherol derivatives of the invention can be used in emulsion compositions.

In one embodiment, the tocopherol derivatives of the invention include a tocopherol moiety covalently coupled to a branched hydrophilic moiety. The branched hydrophilic moiety can include one or more branches. For example, in one embodiment, the branched hydrophilic moiety has a "Y" structure, and in another embodiment, the branched hydrophilic moiety has an "X" structure. Representative tocopherol derivatives of the invention having a "Y" structure are illustrated in FIGS. 1–4. It will be appreciated that other configurations of the tocopherol derivatives of the invention are possible and are within the scope of this invention.

In other embodiments, the tocopherol derivatives of the invention include two or more tocopherol moieties covalently linked though one or more hydrophilic moieties. For tocopherol derivatives of the invention that include three or more tocopherol moieties, the derivatives are branched structures. For tocopherol derivatives having three tocopherol moieties, the derivatives have a "Y" structure. See, for example, FIGS. 5–8. For tocopherol derivatives having four tocopherol derivatives, the derivatives have an "X" structure. See, for example, FIGS. 9–12. It will be appreciated that other configurations of the tocopherol derivatives of the invention as possible and are within the scope of this invention.

Because of their branching and their surfactant properties, the tocopherol derivatives of the invention can be referred to as star surfactants.

The branched nature of the tocopherol derivatives of the invention enables these derivatives to be advantageous used not only as an emulsifier to stabilize a micelle, but also as a crosslinker to link the micelles forming a gel-like formulation depending on the surfactant's property of the surfactant.

Representative emulsion compositions that can advantageously include the tocopherol derivatives of the invention include tocopherol-based emulsion compositions. Tocopherol-based emulsion compositions are described in U.S. patent application Ser. Nos. 09/003,173, filed Jan. 5, 1998; 09/317,495, filed May 24, 1999; 09/317,499, filed May 24, 1999; 09/361,935, filed Jul. 27, 1999; 09/670,627, filed Sep. 27, 2000; each expressly incorporated herein by reference in its entirety. The noted applications describe the use of tocopherol-based emulsions as vehicles for therapeutic drug delivery.

The tocopherol derivatives of the invention can be formulated to provide emulsion vehicles for the delivery of active agents (e.g., therapeutic drugs). Aqueous formulations made using the tocopherol derivatives of the invention can be utilized to carry both lipophilic agents (i.e., oil soluble and water insoluble agents) and hydrophilic agents (i.e., oil insoluble and water soluble agents). Therefore, the surfactants are expected to have many applications in pharmaceuticals and cosmetics.

As noted above, in one embodiment, the present invention provides a tocopherol derivative covalently linked to a branched hydrophilic moiety and, in another embodiment, a tocopherol derivative having two or more tocopherol moieties covalently linked through one or more hydrophilic moieties. Suitable tocopherol compounds that can be incorporated as moieties into the tocopherol derivatives of the invention include any tocopherol compound that can be combined with a hydrophilic compound to provide a tocopherol derivative having surfactant properties. Suitable tocopherol compounds include α-tocotrienol, β-tocotrienol, γ-tocotrienol, δ-tocotrienol, α-tocopherol, α-tocopherol succinate, and α-tocopherol glutarate, among others.

The tocopherol derivatives of the invention can include one or more tocopherol moieties. In one embodiment, the derivative includes two tocopherol moieties. In another embodiment, the derivative includes three tocopherol moieties. In a further embodiment, the derivative includes four tocopherol moieties. It will be appreciated that highly branched derivatives can be made, that these derivatives can include more than four tocopherol derivatives, and that these derivatives are within the scope of the invention.

The tocopherol derivatives of the invention include one or more hydrophilic moieties. For embodiments that include more than one tocopherol moiety, the hydrophilic moieties are the "branches" linking the tocopherol moieties. In the tocopherol derivative, the tocopherol moiety is located at the branch terminus.

In the tocopherol derivatives, the hydrophilic moiety can be covalently coupled directly to the tocopherol moiety. Alternatively, the hydrophilic moiety can be covalently coupled to the tocopherol moiety through one or more functional groups (e.g., linker moieties). See, for example, FIGS. 1 and 3–12 in which the hydrophilic moiety is covalently coupled to the tocopherol moiety through a succinic acid link (i.e., a succinic diester link). Referring to FIG. 2, the hydrophilic moiety is covalently coupled to the tocopherol moiety through an ether link (i.e., a diether link). It will be appreciated that other dicarboxylic acids (e.g., glutaric acid, methyl succinic acid, dicarboxy amino acids), other diethers, as well as other linkers, can be used to covalently couple the hydrophilic moiety and the tocopherol moiety to provide the tocopherol derivative of the invention. In FIGS. 1 and 5–12, the X refers to a succinic acid linkage. Other suitable linkages include, for example, carbon—carbon, amine, ether, ester, amide, thio ether, thio ester, and thio amide links, among others.

Suitable hydrophilic moieties include any hydrophilic moiety that, when covalently coupled to a tocopherol moiety, provides the tocopherol derivative with surfactant properties. The hydrophilic moiety generally includes polar functional groups, for example, ether and amine functional groups. In one embodiment, the hydrophilic moiety is a polyether. In one embodiment, the hydrophilic group includes a poly(oxyethylene) group, —(CH$_2$CH$_2$O)$_n$—. In another embodiment, the hydrophilic group includes a poly(oxypropylene) group, —(CH$_2$CH$_2$CH$_2$O)$_m$—. In another embodiment, the hydrophilic group includes a poly(oxyethylene) group and a poly(oxypropylene) group. In the figures, the poly(oxypropylene) group is designated —(C$_3$H$_6$O)$_m$—.

Figure 9:
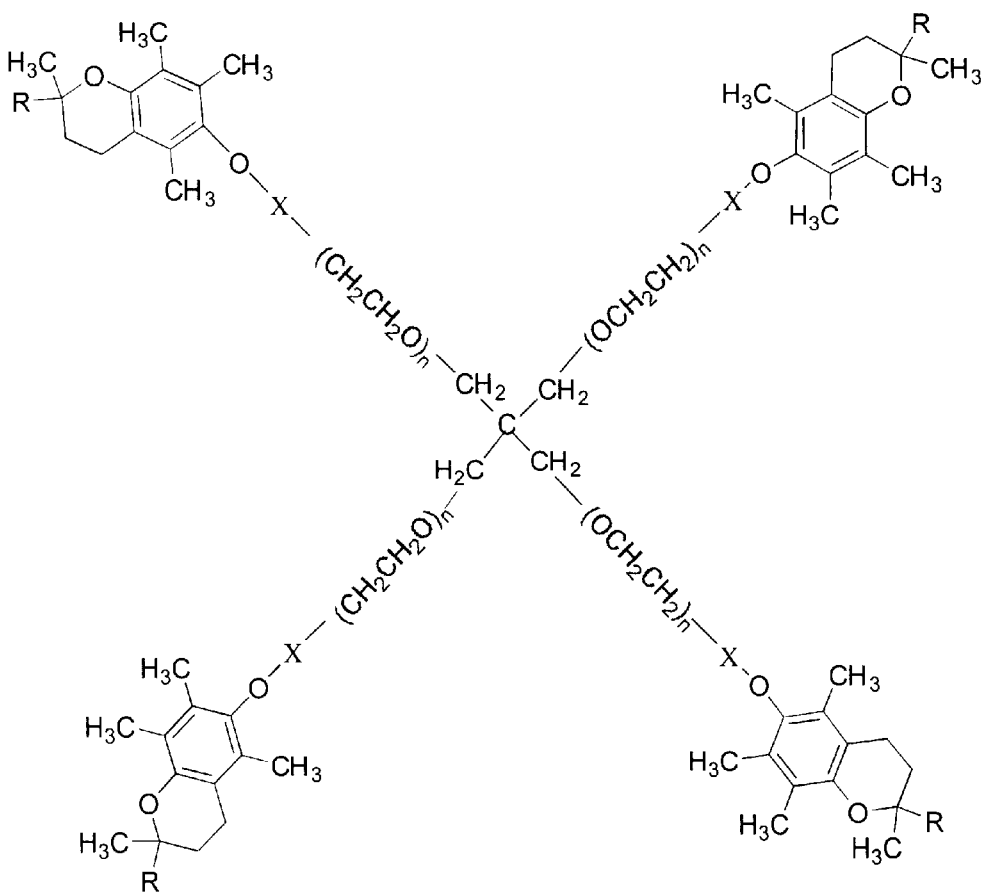
FIG. 9 is the structure of a representative tocopherol derivative of the present invention including four tocopherol moieties linked through poly(oxyethylene) moieties.
Figure 10:
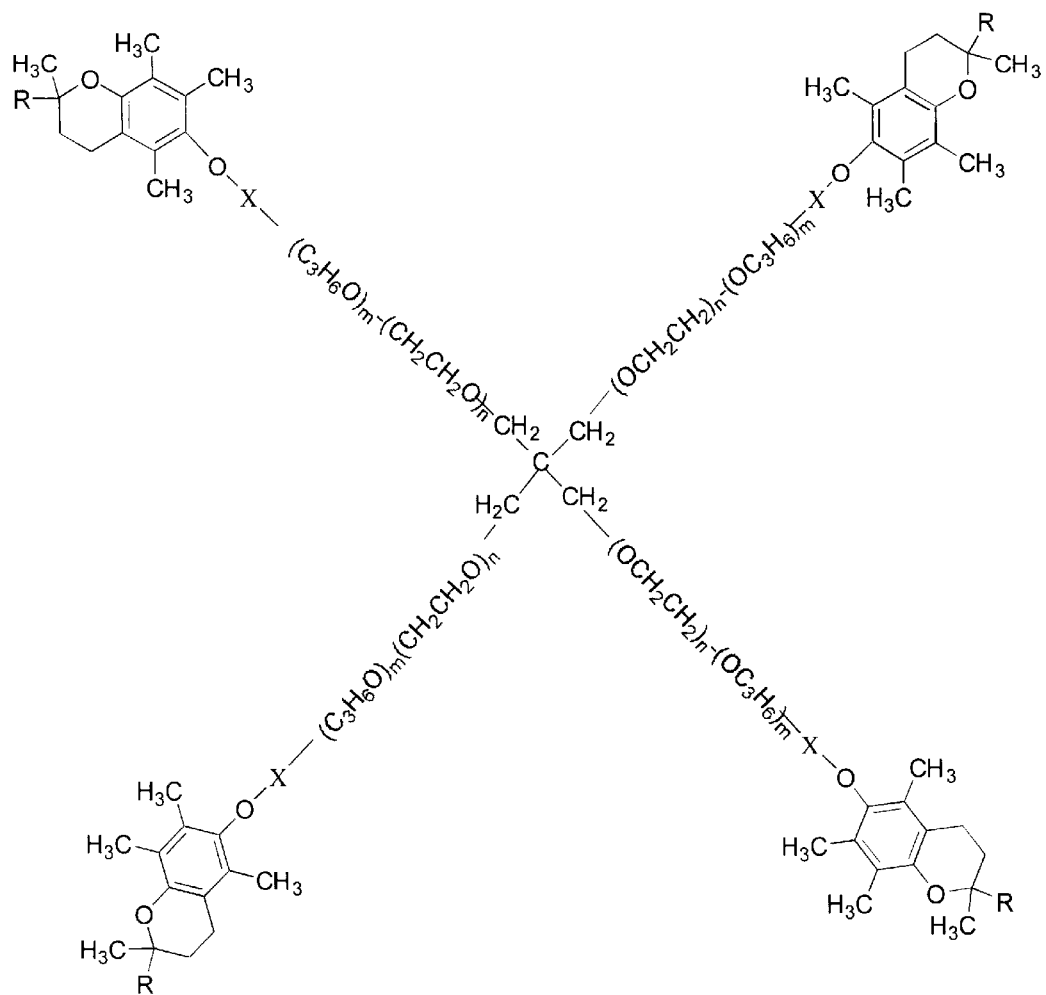
FIG. 10 is the structure of a representative tocopherol derivative of the present invention including four tocopherol moieties linked through poly(oxyethylene) and poly(oxypropylene) moieties.
Figure 11:
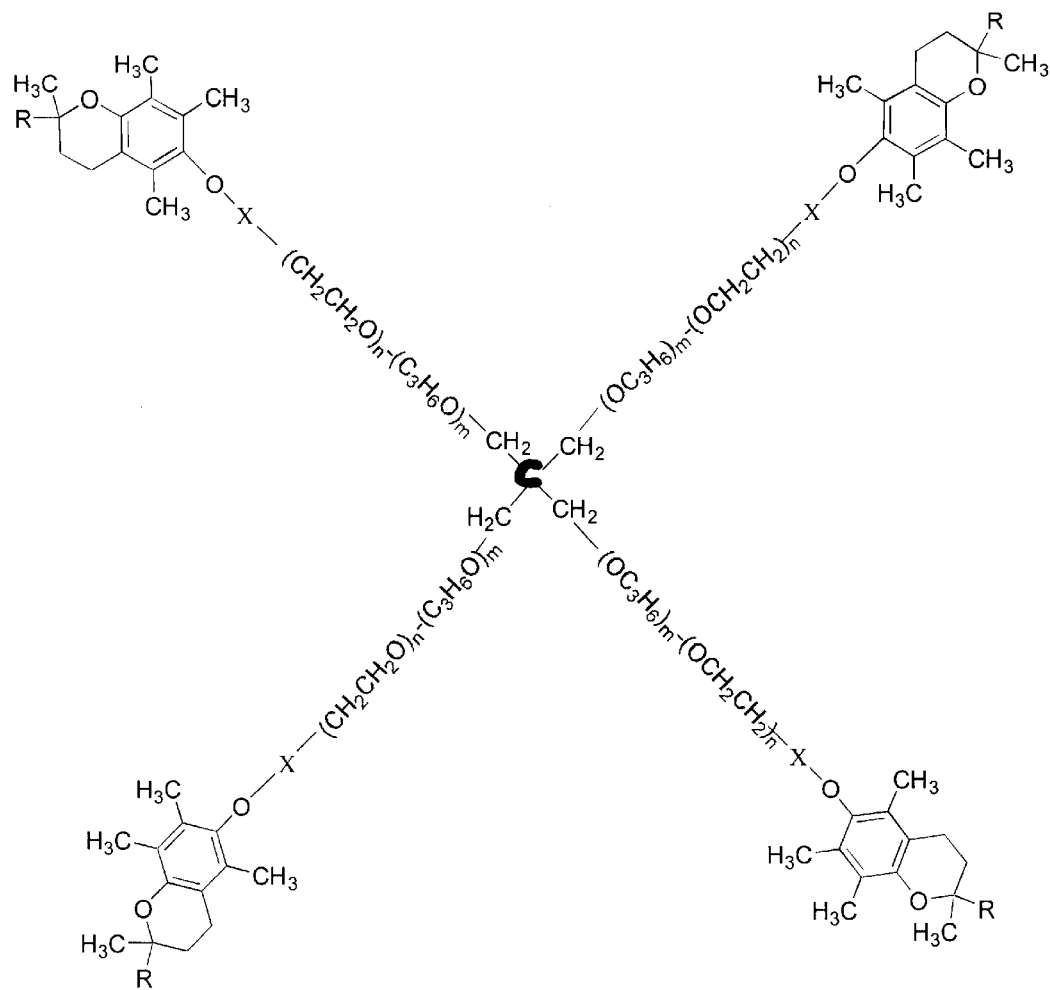
FIG. 11 is the structure of a representative tocopherol derivative of the present invention including four tocopherol moieties linked through poly(oxyethylene) and poly(oxypropylene) moieties.

In the tocopherol derivatives, the hydrophilic moieties can be joined through a core moiety. Generally, the core moiety is a multifunctional moiety from which the hydrophilic branches emanate. In certain embodiments, the one or more branches ultimately terminate with a tocopherol moiety. For example, referring to FIG. 1, in this representative tocopherol derivative, the core moiety includes an isopropyl radical (i.e., glycerol), the hydrophilic moiety includes a poly(oxyethylene) moiety, and the tocopherol moiety is α-tocopherol. The tocopherol moiety is coupled to the poly(oxyethylene) through a succinic diester link. In FIG. 9, the representative tocopherol derivative has a core moiety that includes a neopentyl radical (i.e., pentaerythritol), a hydrophilic moiety that includes a poly(oxyethylene) moiety, and a tocopherol moiety that is α-tocopherol. The tocopherol moieties are coupled to the poly(oxyethylene) groups through a succinic diester link.

It will be appreciated that the core moiety can be covalently coupled to the hydrophilic moiety, either directly or indirectly, by any one of a variety of chemical linkages including, for example, carbon—carbon, amine, ether, ester, amide, thio ether, thio ester, and thio amide linkages, among others.

Figure 2:
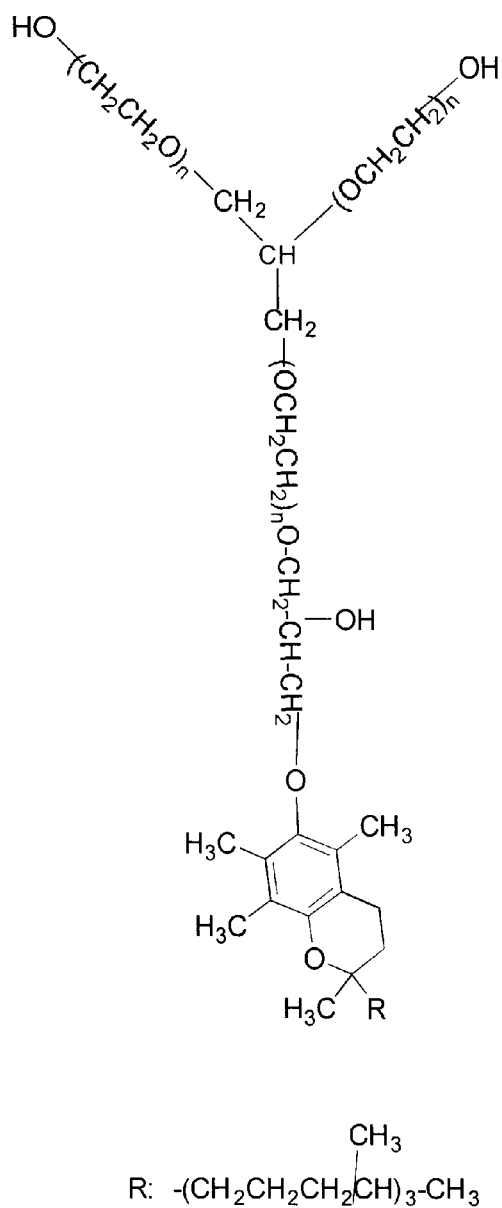
FIG. 2 is the structure of a representative tocopherol derivative of the present invention including a tocopherol moiety linked to a branched poly(oxyethylene)-containing hydrophilic moiety through an ether group.
Figure 3:
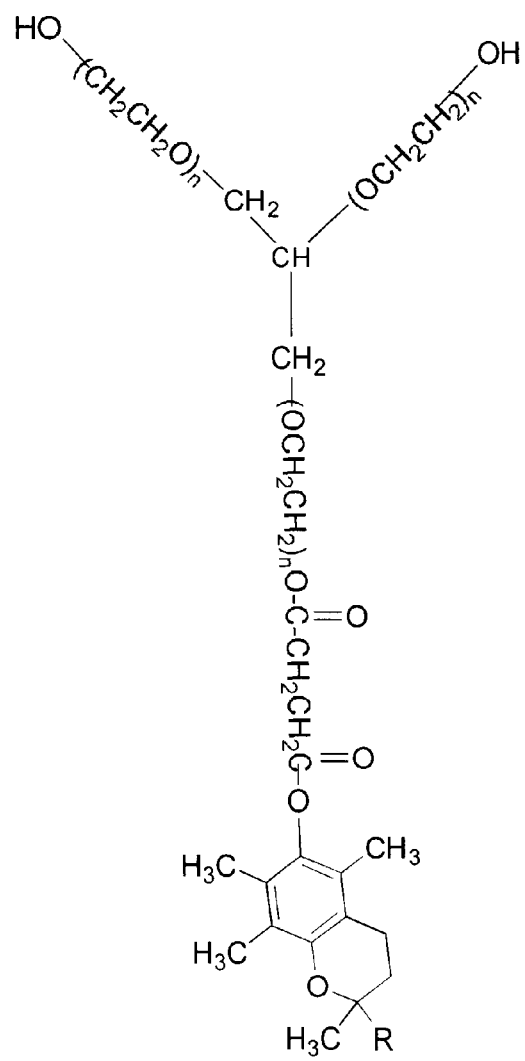
FIG. 3 is the structure of a representative tocopherol derivative of the present invention including a tocopherol moiety linked to a branched poly(oxyethylene)-containing hydrophilic moiety through an ester group.
Figure 3:
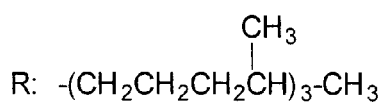
Figure 4:
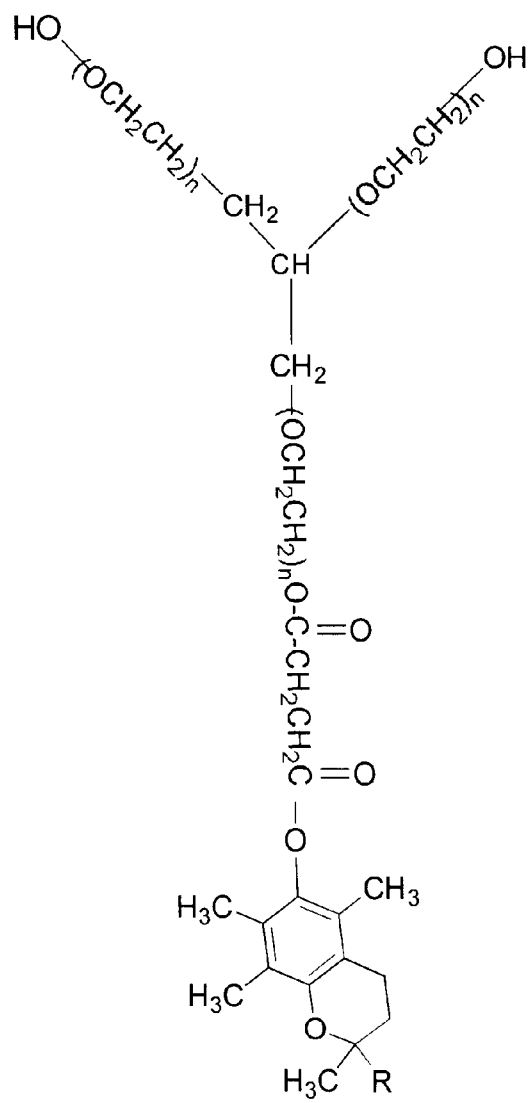
FIG. 4 is the structure of a representative tocopherol derivative of the present invention including a tocopherol moiety linked to a branched poly(oxyethylene)-containing hydrophilic moiety through an ester group.
Figure 4:
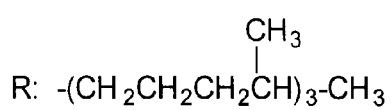
Figure 5:
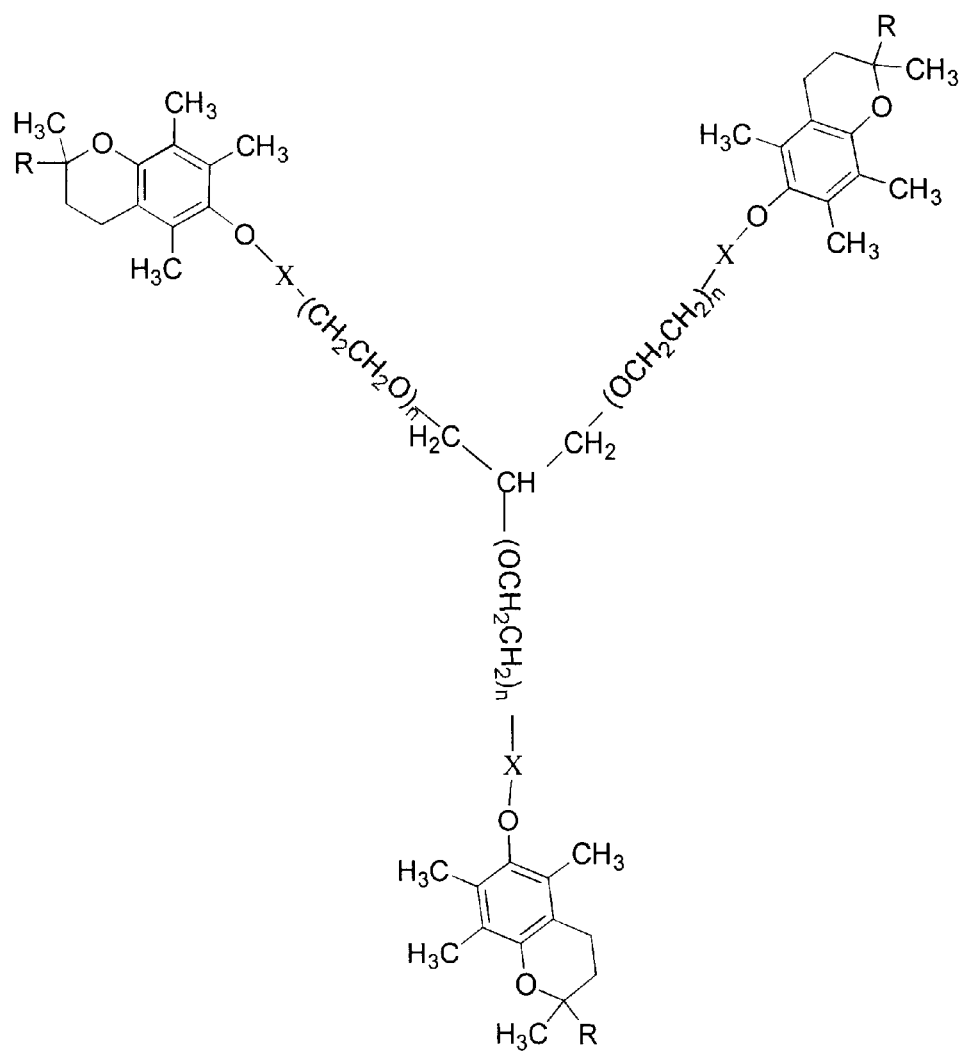
FIG. 5 is the structure of a representative tocopherol derivative of the present invention including three tocopherol moieties linked through poly(oxyethylene) moieties.
Figure 8:
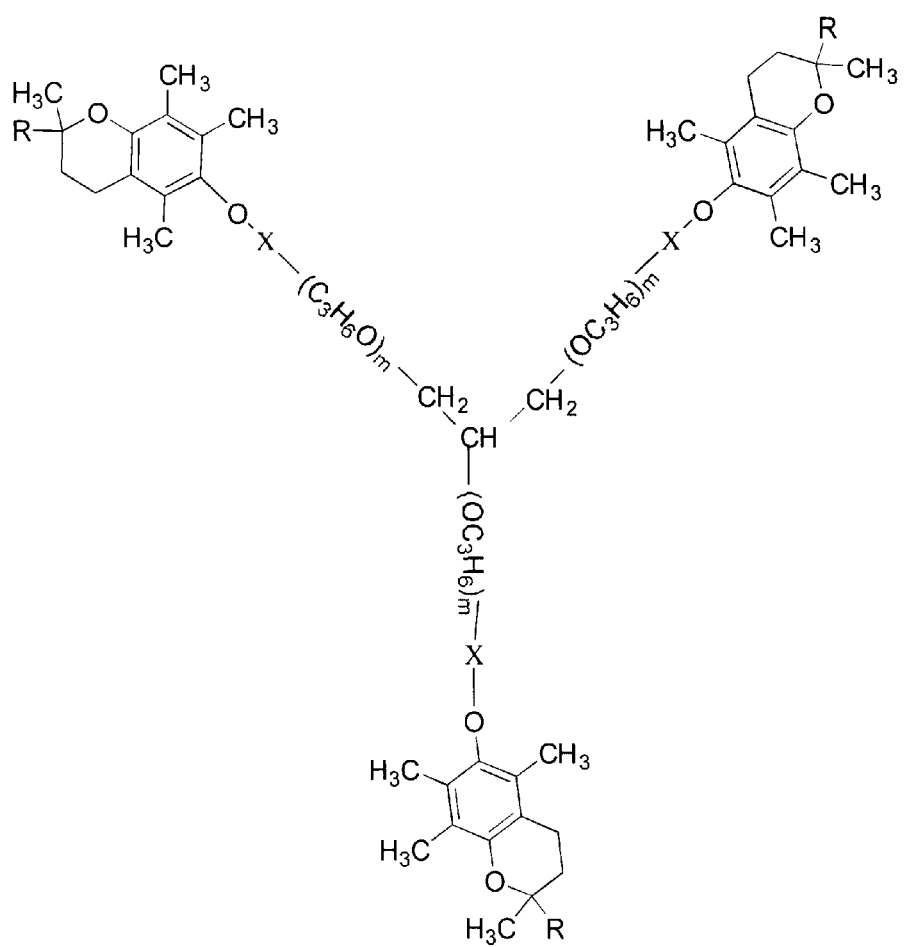
FIG. 8 is the structure of a representative tocopherol derivative of the present invention including three tocopherol moieties linked through poly(oxypropylene) moieties.
Figure 12:
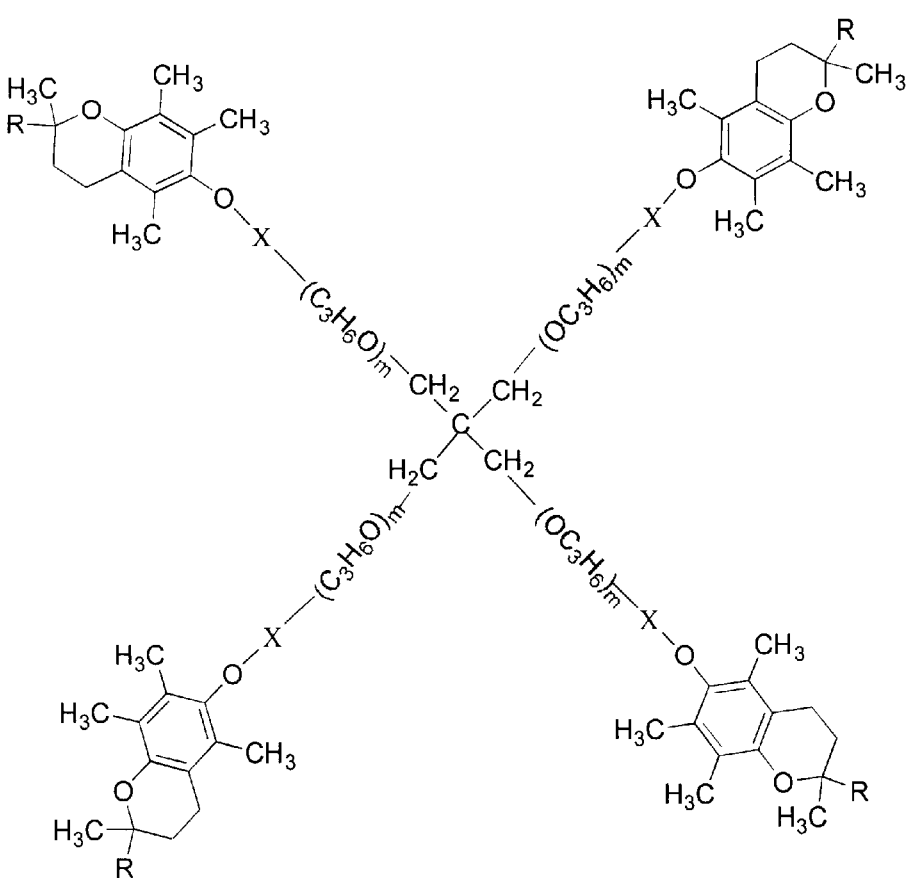
FIG. 12 is the structure of a representative tocopherol derivative of the present invention including four tocopherol moieties linked through poly(oxypropylene) moieties.

Representative tocopherol derivatives of the invention are illustrated in FIGS. 1–12. These representative derivatives include poly(oxyethylene) and/or poly(oxypropylene) groups. In FIGS. 1, 5, and 9, n=6 to 70. In FIGS. 2 and 3, n=7–8. In FIG. 4, n=30. In FIGS. 6, 7, 10, and 11, n=6–50 and m=6–50. In FIGS. 8 and 12, m=6–60.

The preparations of representative tocopherol derivatives having a tocopherol moiety covalently coupled to a branched poly(oxyethylene)-containing hydrophilic moiety are described in Examples 1–3. The preparation of a representative tocopherol derivative having three tocopherol moieties linked through poly(oxyethylene) and poly(oxypropylene) moieties is described in Example 4.

As noted above, in one embodiment, the present invention provides a tocopherol derivative covalently coupled to a branched hydrophilic moiety. The tocopherol moiety and hydrophilic moiety can be covalently coupled through a linker moiety (e.g., succinic diester). The tocopherol derivative can include a core moiety from which the hydrophilic moieties branch. The core moiety can be covalently coupled to the hydrophilic moiety through a linker moiety.

In one embodiment, the tocopherol derivative has the structure:

E-L-C(L)n where n=2 or 3.

In another embodiment, the tocopherol derivative has the structure:

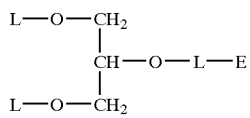

In a further embodiment, the tocopherol derivative has the structure:

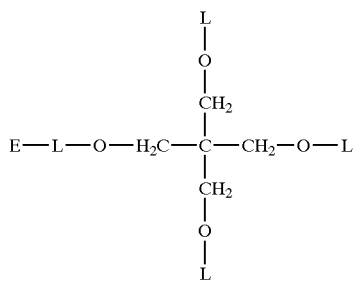

In these structures, E refers to a tocopherol derivative, L refers to a hydrophilic moiety, and C refers to a core moiety, all of which are as described above.

In another embodiment, the present invention provides a tocopherol derivative having a first tocopherol moiety covalently coupled to a second tocopherol moiety through a hydrophilic moiety. The tocopherol derivative and hydrophilic moiety can be covalently coupled through a linker moiety (e.g., succinic diester). Depending on the nature of the hydrophilic moiety, the tocopherol derivative can include two, three, four, or more tocopherol moieties. The tocopherol derivative can include a core moiety from which the hydrophilic moieties branch. The core moiety can be covalently coupled to the hydrophilic moiety through a linker moiety.

In one embodiment, the tocopherol derivative has the structure:

(E-L)$_n$C where n=2–4.

In another embodiment, the tocopherol derivative has the structure:

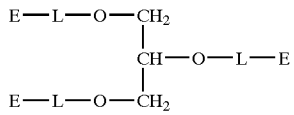

In a further embodiment, the tocopherol derivative has the structure:

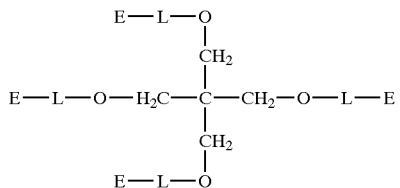

In these structures, E refers to a tocopherol derivative, L refers to a hydrophilic moiety, and C refers to a core moiety, all of which are as described above.

The following examples are provided for the purpose of illustrating, not limiting the present invention.

EXAMPLES

Example 1

The Preparation of DL-α-Tocopherol Glycerol Ethoxylate (1,000): Diether Link

In this example, the preparation of a representative tocopherol derivative of the invention, a tocopherol derivative having a tocopherol moiety linked to a branched poly(oxyethylene)-containing hydrophilic moiety, is described. The structure of the representative tocopherol derivative is illustrated in FIG. 2.

To a 250 ml flask containing 150 ml 1,4-dioxane was added 17.2 g of DL-α-tocopherol, 11.2 g of epibromohydrin, and 2.24 g of potassium hydroxide. The mixture was stirred at reflux for 20 hours. The solvent was removed under reduced pressure and the product dried under vacuum. The resulting oily residue was extracted with ethyl acetate. The organic phase was washed with water for three times. The ethyl acetate was removed to provide 18.5 g of (2,3-epoxypropane)tocopherol (94.9% yield).

The (2,3-epoxypropane)tocopherol (2.44 g) obtained above was dissolved into 10 ml of 1,4-dioxane in a 25 ml flask. To the mixture was added 5.0 g of glycerol ethoxylate (M. W. 1,000) and 0.28 g of potassium hydroxide, and the mixture was stirred at 100° C. for 20 hours. The mixture was cooled to room temperature, and the solvent was removed under reduced pressure. The residue was dissolved in dichloromethane, and washed with water for three times. The solution was dried over magnesium sulfate anhydrous, filtered, and solvent was removed under vacuum. Tocopherol-glycerol ethoxylate was obtained in 75.2% yield.

Example 2

The Preparation of DL-α-Tocopherol Glycerol

Ethoxylate (1,000): Succinate Diester Link

In this example, the preparation of a representative tocopherol derivative of the invention, a tocopherol derivative having a tocopherol moiety linked to a branched poly (oxyethylene)-containing hydrophilic moiety, is described. The structure of the representative tocopherol derivative is illustrated in FIG. 3.

To a 250 ml flask was added 10.61 g of vitamin E succinate, 20.00 of glycerol ethoxylate (M. W. 1,000), 4.20 g of N,N'-dicyclohexylcarbodiimide, 100 mg of 4-dimethylaminopyridine, and 100 ml of chloroform. The mixture was stirred at reflux overnight (about 20 hours). The mixture was filtered to remove precipitate. Solvent was removed under reduced pressure. The residue was dissolved in 100 ml of ethyl acetate-hexane solution to further precipitate dicyclohexylurea. The mixture was filtered to remove the precipitate. The solvent was then removed under reduced pressure. The residue was extracted three times with hexane-diethyl ether (5:1 v/v), and then dried under vacuum to provide the product as an oil (92.9% yield).

Example 3

The Preparation of DL-α-Tocopherol Glycerol Ethoxylate (4,000): Succinate Diester Link In this example, the preparation of a representative tocopherol derivative of the invention, a tocopherol derivative having a tocopherol moiety linked to a branched poly (oxyethylene)-containing hydrophilic moiety, is described. The structure of the representative tocopherol derivative is illustrated in FIG. 4.

To a 250 ml flask was added 4.00 g of vitamin E succinate, 10.00 of glycerol ethoxylate (M. W. 4,000), 1.55 g of N,N'-dicyclohexylcarbodiimide, 50 mg of 4-dimethylaminopyridine, and 100 ml of tetrahydrofuran. The mixture was stirred at reflux overnight (about 20 hours). After cooling to room temperature, the mixture was filtered to remove the solid phase. Solvent was removed under reduced pressure. The residue was dissolved in 100 ml of ethyl acetate-hexane solution to further precipitate dicyclohexylurea. The mixture was filtered to remove the precipitate. The solvent was then removed under reduced pressure. The residue was extracted three times with hexane-diethyl ether (5:1 v/v), and then dried with vacuum to yield the product as an oil (63.3% yield).

Example 4
The Preparation of DL-α-Tocopherol Glycerol Proxylate-b-Ethoxylate (4,000)

Figure 6:
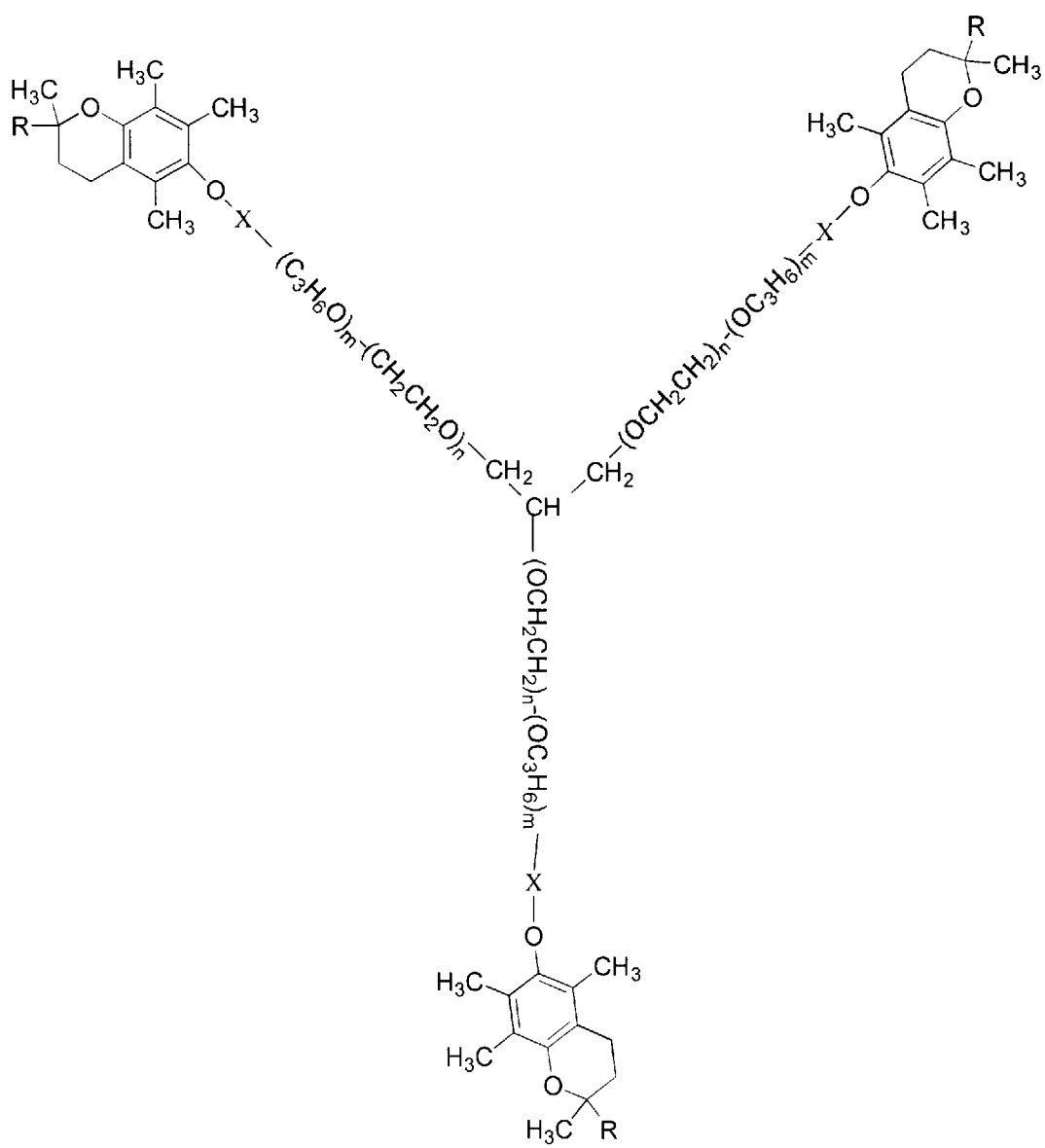
FIG. 6 is the structure of a representative tocopherol derivative of the present invention including three tocopherol moieties linked through poly(oxyethylene) and poly(oxypropylene) moieties.
Figure 7:
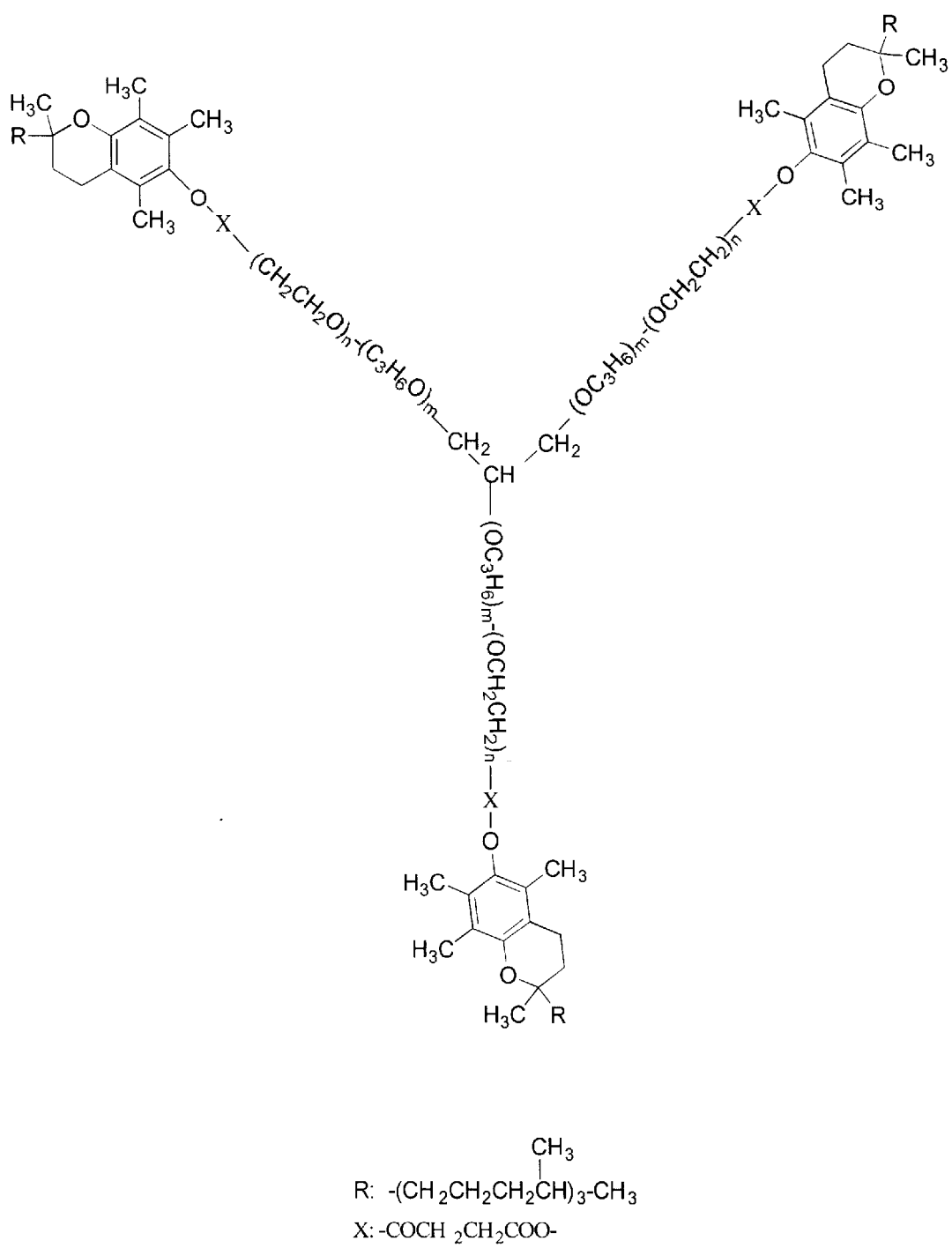
FIG. 7 is the structure of a representative tocopherol derivative of the present invention including three tocopherol moieties linked through poly(oxyethylene) and poly(oxypropylene) moieties.

In this example, the preparation of a representative tocopherol derivative of the invention, a tocopherol derivative having three tocopherol moieties linked through poly (propoxylate-b-ethoxylate) (i.e., poly(oxypropylene) and poly(oxyethylene) moieties), is described. The structure of the representative tocopherol derivative is illustrated in FIG. 6.

To a 250 ml flask was added 3.32 g of vitamin E succinate, 10.0 g of glycerol propoxylate-b-ethoxylate (M. W. 4,000, functionality 2.5), 1.30 g of N,N'-dicyclohexylcarbodiimide, 50 mg of 4-dimethylaminopyridine, and 100 ml of chloroform. The mixture was stirred at reflux overnight ( about 20 hours). After cooling to room temperature, the mixture was filtered to remove the solid phase. Solvent was removed under reduced pressure. The residue was dissolved in 100 ml of ethyl acetate-hexane solution to further precipitate dicyclohexylurea. The mixture was filtered again to remove the precipitate. The solvent was then removed under reduced pressure. The residue was extracted three times with a diethyl ether-hexane solution (2:1 v/v), and then dried under vacuum to yield the product as an oil (71.0% yield).

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A compound, comprising a first tocopherol moiety covalently coupled to a second tocopherol moiety through a branched hydrophilic moiety.

2. The compound of claim 1, wherein the tocopherol moiety is covalently coupled to the hydrophilic moiety through a linker moiety.

3. The compound of claim 2, wherein the linker moiety comprises a succinate diester moiety.

4. The compound of claim 1, wherein the hydrophilic moiety comprises a poly(oxyethylene) moiety.

5. The compound of claim 1, wherein the hydrophilic moiety comprises a poly(oxypropylene) moiety.

6. The compound of claim 1, wherein the hydrophilic moiety comprises a poly(oxyethylene) moiety and a poly(oxypropylene) moiety.

7. The compound of claim 1, further comprising a third tocopherol moiety.

8. The compound of claim 7, wherein the third tocopherol moiety is covalently coupled through a hydrophilic moiety.

9. The compound of claim 7 further comprising a fourth tocopherol moiety.

10. The compound of claim 9, wherein the fourth tocopherol moiety is covalently coupled through a hydrophilic moiety.

11. The compound of claim 1, wherein the first and second tocopherol moieties is at least one of α-tocotrienol, β-tocotrienol, γ-tocotrienol, δ-tocotrienol, and α-tocopherol.

12. A compound having the structure:

wherein E comprises a tocopherol moiety;

wherein L comprises a hydrophilic moiety;

wherein C comprises a core moiety; and wherein n=3 or 4.

13. The compound of claim 12, wherein the hydrophilic moiety comprises a poly(oxyethylene) moiety.

14. The compound of claim 12, wherein the hydrophilic moiety comprises a poly(oxypropylene) moiety.

15. The compound of claim 12, wherein the hydrophilic moiety comprises a poly(oxyethylene) moiety and a poly(oxypropylene) moiety.

16. The compound of claim 12, wherein the core moiety comprises an isopropyl radical.

17. The compound of claim 12, wherein the core moiety comprises a neopentyl radical.

18. The compound of claim 12, wherein the tocopherol moiety is at least one of α-tocotrienol, β-tocotrienol, γ-tocotrienol, δ-tocotrienol, and α-tocopherol.

19. The compound of claim 12 further comprising a linker moiety covalently coupling the tocopherol moiety and the hydrophilic moiety.

20. The compound of claim 19, wherein the linker moiety comprises a succinic diester moiety.

21. A compound having the structure:

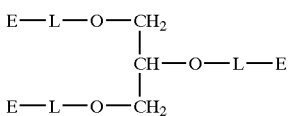

wherein E comprises a tocopherol moiety; and
wherein L comprises a hydrophilic moiety.

22. The compound of claim 21, wherein the hydrophilic moiety comprises a poly(oxyethylene) moiety.

23. The compound of claim 21, wherein the hydrophilic moiety comprises a poly(oxypropylene) moiety.

24. The compound of claim 21, wherein the hydrophilic moiety comprises a poly(oxyethylene) moiety and a poly(oxypropylene) moiety.

25. The compound of claim 21, wherein the tocopherol moiety is at least one of α-tocotrienol, β-tocotrienol, γ-tocotrienol, δ-tocotrienol, and α-tocopherol.

26. The compound of claim 21 further comprising a linker moiety covalently coupling the tocopherol moiety and the hydrophilic moiety.

27. The compound of claim 26, wherein the linker moiety comprises a succinic diester moiety.

28. A compound having the structure:
wherein E comprises a tocopherol moiety; and

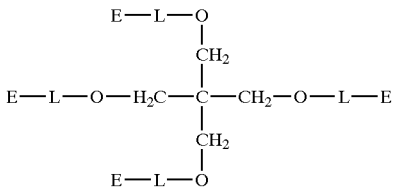

wherein L comprises a hydrophilic moiety.

29. The compound of claim 28, wherein the hydrophilic moiety comprises a poly(oxyethylene) moiety.

30. The compound of claim 28, wherein the hydrophilic moiety comprises a poly(oxypropylene) moiety.

31. The compound of claim 28, wherein the hydrophilic moiety comprises a poly(oxyethylene) moiety and a poly(oxypropylene) moiety.

32. The compound of claim 28, wherein the tocopherol moiety is at least one of α-tocotrienol, β-tocotrienol, γ-tocotrienol, δ-tocotrienol, and α-tocopherol.

33. The compound of claim 28 further comprising a linker moiety covalently attaching the tocopherol moiety and the hydrophilic moiety.

34. The compound of claim 33, wherein the linker moiety comprises a succinic diester moiety.

35. A compound, comprising a tocopherol moiety covalently coupled to a branched hydrophilic moiety.

36. The compound of claim 35, wherein the tocopherol moiety is covalently coupled to the hydrophilic moiety through a linker moiety.

37. The compound of claim 36, wherein the linker moiety comprises a succinate diester moiety.

38. The compound of claim 35, wherein the hydrophilic moiety comprises a poly(oxyethylene) moiety.

39. The compound of claim 35, wherein the hydrophilic moiety comprises a poly(oxypropylene) moiety.

40. The compound of claim 35, wherein the hydrophilic moiety comprises a poly(oxyethylene) moiety and a poly(oxypropylene) moiety.

41. The compound of claim 35, wherein the tocopherol moiety is at least one of α-tocotrienol, β-tocotrienol, γ-tocotrienol, δ-tocotrienol, and α-tocopherol.

42. A compound having the structure:

E-L-C(L)n wherein E comprises a tocopherol moiety;

wherein L comprises a hydrophilic moiety;

wherein C comprises a core moiety; and wherein n=2 or 3.

43. The compound of claim 42, wherein the hydrophilic moiety comprises a poly(oxyethylene) moiety.

44. The compound of claim 42, wherein the hydrophilic moiety comprises a poly(oxypropylene) moiety.

45. The compound of claim 42, wherein the hydrophilic moiety comprises a poly(oxyethylene) moiety and a poly(oxypropylene) moiety.

46. The compound of claim 42, wherein the core moiety comprises an isopropyl radical.

47. The compound of claim 42, wherein the core moiety comprises a neopentyl radical.

48. The compound of claim 42, wherein the tocopherol moiety is at least one of α-tocotrienol, β-tocotrienol, γ-tocotrienol, δ-tocotrienol, and α-tocopherol.

49. The compound of claim 42 further comprising a linker moiety covalently coupling the tocopherol moiety and the hydrophilic moiety.

50. The compound of claim 49, wherein the linker moiety comprises a succinic diester moiety.

51. A compound having the structure:

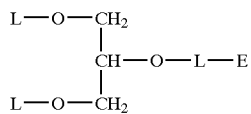

wherein E comprises a tocopherol moiety; and wherein L comprises a hydrophilic moiety.

52. The compound of claim 51, wherein the hydrophilic moiety comprises a poly(oxyethylene) moiety.

53. The compound of claim 51, wherein the hydrophilic moiety comprises a poly(oxypropylene) moiety.

54. The compound of claim 51, wherein the hydrophilic moiety comprises a poly(oxyethylene) moiety and a poly(oxypropylene) moiety.

55. The compound of claim 51, wherein the tocopherol moiety is at least one of α-tocotrienol, β-tocotrienol, γ-tocotrienol, δ-tocotrienol, and α-tocopherol.

56. The compound of claim 51 further comprising a linker moiety covalently coupling the tocopherol moiety and the hydrophilic moiety.

57. The compound of claim 56, wherein the linker moiety comprises a succinic diester moiety.

58. A compound having the structure:

wherein E comprises a tocopherol moiety; and

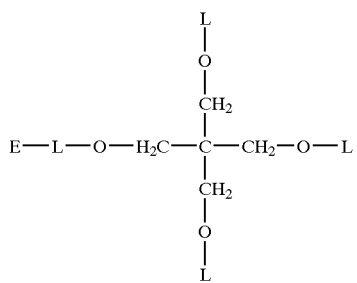

wherein L comprises a hydrophilic moiety.

59. The compound of claim 58, wherein the hydrophilic moiety comprises a poly(oxyethylene) moiety.

60. The compound of claim 58, wherein the hydrophilic moiety comprises a poly(oxypropylene) moiety.

61. The compound of claim 58, wherein the hydrophilic moiety comprises a poly(oxyethylene) moiety and a poly(oxypropylene) moiety.

62. The compound of claim 58, wherein the tocopherol moiety is at least one of α-tocotrienol, β-tocotrienol, γ-tocotrienol, δ-tocotrienol, and α-tocopherol.

63. The compound of claim 58 further comprising a linker moiety covalently coupling the tocopherol moiety and the hydrophilic moiety.

64. The compound of claim 63, wherein the linker moiety comprises a succinic diester moiety.

* * * * *

UNITED STATES PATENT AND TRADEMARK OFFICE
CERTIFICATE OF CORRECTION

PATENT NO. : 6,683,194 B2
DATED : January 27, 2004
INVENTOR(S) : Y. Zhang et al.

It is certified that error appears in the above-identified patent and that said Letters Patent is hereby corrected as shown below:

<u>Title page,</u>
Item [57], ABSTRACT,
Line 3, "to branched" should read -- to a branched --

<u>Column 8,</u>
Line 16, "succinate" should read -- succinic --
Line 28, "claim 7" should read -- claim 7, --
Line 35, "moieties is" should read -- moieties are --
Line 62, "claim 12" should read -- claim 12, --

<u>Column 9,</u>
Line 21, "claim 21" should read -- claim 21, --
Line 27, delete the clause "wherein E comprises a tocopherol moiety; and"; then insert the clause -- wherein E comprises a tocopherol moiety; and -- after the formula and before the clause "wherein L comprises a hydrophilic moiety."
Line 49, "claim 28" should read -- claim 28, --

<u>Column 10,</u>
Line 34, "claim 42" should read -- claim 42, --
Line 62, "claim 51" should read -- claim 51, --

<u>Column 11,</u>
Line 2, delete the clause "wherein E comprises a tocopherol moiety; and"; then insert the clause -- wherein E comprises a tocopherol moiety; and -- after the formula and before the clause "wherein L comprises a hydrophilic moiety."

UNITED STATES PATENT AND TRADEMARK OFFICE
CERTIFICATE OF CORRECTION

PATENT NO. : 6,683,194 B2
DATED : January 27, 2004
INVENTOR(S) : Y. Zhang et al.

It is certified that error appears in the above-identified patent and that said Letters Patent is hereby corrected as shown below:

Column 12,
Line 11, "claim 58" should read -- claim 58, --

Signed and Sealed this

Sixth Day of July, 2004

JON W. DUDAS
*Acting Director of the United States Patent and Trademark Office*